United States Patent [19]
Hendriks et al.

[11] Patent Number: 6,166,184
[45] Date of Patent: Dec. 26, 2000

[54] PROCESS FOR MAKING A BIOPROSTHETIC DEVICE

[75] Inventors: Marc Hendriks, Brunssum; Verhoeven Michel, Maastricht; Patrick Cahalan, Geleen, all of Netherlands; Mark W. Torrianni, San Juan Capistrano, Calif.; Linda Cahalan, Geleen, Netherlands; Benedicte Fouache, Lille, France

[73] Assignee: Medtronic Inc., Minneapolis, Minn.

[21] Appl. No.: 08/912,778

[22] Filed: Aug. 18, 1997

[51] Int. Cl.⁷ .......................... C07K 13/00; C07K 15/00
[52] U.S. Cl. .................... 530/356; 530/402; 525/54.1; 8/94.11; 623/1; 623/2; 623/3; 623/11; 523/113
[58] Field of Search ................. 530/356, 402; 525/54.1; 8/94.11; 623/1, 2, 3, 11; 523/113

[56] References Cited

U.S. PATENT DOCUMENTS

| | | | |
|---|---|---|---|
| 4,378,224 | 3/1983 | Nimni et al. | 8/94.11 |
| 4,806,595 | 2/1989 | Noishiki et al. | 525/54.2 |
| 5,080,670 | 1/1992 | Imamura et al. | 623/2 |
| 5,162,430 | 11/1992 | Rhee et al. | 525/54.1 |
| 5,264,214 | 11/1993 | Rhee et al. | 424/422 |
| 5,279,612 | 1/1994 | Eberhardt | 8/94.11 |
| 5,292,802 | 3/1994 | Rhee et al. | 525/54.1 |
| 5,304,595 | 4/1994 | Rhee et al. | 525/54.1 |
| 5,306,500 | 4/1994 | Rhee et al. | 424/422 |
| 5,308,889 | 5/1994 | Rhee et al. | 523/113 |
| 5,324,775 | 6/1994 | Rhee et al. | 525/54.2 |
| 5,328,955 | 7/1994 | Rhee et al. | 525/54.1 |
| 5,352,240 | 10/1994 | Ross | 623/2 |
| 5,376,375 | 12/1994 | Rhee et al. | 424/423 |
| 5,413,791 | 5/1995 | Rhee et al. | 424/422 |
| 5,428,022 | 6/1995 | Palefsky et al. | 514/21 |
| 5,446,091 | 8/1995 | Rhee et al. | 525/54.1 |
| 5,447,536 | 9/1995 | Girardot et al. | 8/94.11 |
| 5,470,911 | 11/1995 | Rhee et al. | 525/54.1 |
| 5,475,052 | 12/1995 | Rhee et al. | 525/54.1 |

*Primary Examiner*—Marianne M. Cintins
*Assistant Examiner*—C. Delacroix-Muirheid
*Attorney, Agent, or Firm*—Thomas F. Woods; Michael J. Jaro; Harold Patton

[57] ABSTRACT

Methods for making bioprosthetic devices made of collagen-based material having collagen amine groups and collagen carboxyl groups are provided. The methods include blocking at least a portion of the collagen amine groups with a blocking agent, activating at least a portion of the collagen carboxyl groups after blocking at least a portion of the collagen amine groups to form activated carboxyl groups, and contacting the activated collagen carboxyl groups with a polyfunctional spacer to crosslink the collagen-based material.

42 Claims, 5 Drawing Sheets

PROCESS FOR MAKING A BIOPROSTHETIC DEVICE

BACKGROUND OF THE INVENTION

Prosthetic implants, which can be made from natural or synthetic materials, include, for example, heart valves, vascular grafts, urinary bladder prostheses, and tendon prostheses. Bioprostheses (i.e., prostheses derived from natural tissue) are typically preferred over synthetic or mechanical prostheses. For example, natural tissue valves are preferred over mechanical valves because tissue valves stimulate the natural flow of the blood better than mechanical valves. Also, no blood anticoagulants are needed when natural tissue valves are used.

Tissue heart valve prostheses are typically made from either porcine aortic valves or bovine pericardium. Such valves are typically made by pretreating the tissue with glutaraldehyde or other crosslinking agent, as discussed below, and sewing the tissue into a flexible metallic alloy or polymeric stent. Such animal tissues mainly consist of collagen and elastin. These components provide the tissues, particularly heart valves, with their needed mechanical strength and flexibility.

Collagen-based materials, including whole tissue, are finding increased use in the manufacture of biomedical devices, such as prosthetic implants. This is particularly true for heart valves. Collagen is a naturally occurring protein featuring good biocompatibility. It is the major structural component of vertebrates, forming extracellular fibers or networks in practically every tissue of the body, including skin, bone, cartilage, and blood vessels. In medical devices, collagen provides a more physiological, isotropic environment that has been shown to promote the growth and function of different cell types, facilitating the rapid overgrowth of host tissue after implantation.

Basically, three types of collagen-based materials can be identified, based on the differences in the purity and integrity of the collagen fiber bundle network initially present in the material. The first type includes whole tissue including noncollagenous substances or cells. As a result of using whole tissue, the naturally occurring composition and the native strength and structure of the collagen fiber bundle network are preserved. Whole tissue xenografts have been used in construction of heart valve prostheses, and also in vascular prostheses. However, the presence of soluble proteins, glycoproteins, glycosaminoglycans, and cellular components in such whole tissue xenografts may induce an immunological response of the host organism to the implant.

The second type of collagen-based material includes only the collagen matrix without the noncollagenous substances. The naturally occurring structure of the collagen fiber bundle network is thus preserved, but the antigenicity of the material is reduced. The fibrous collagen materials obtained by removing the antigenic noncollagenous substances will generally have suitable mechanical properties.

The third type of collagen-based material is purified fibrous collagen. Purified collagen is obtained from whole tissue by first dispersing or solubilizing the whole tissue by either mechanical or enzymatic action. The collagen dispersion or solution is then reconstituted by either air drying, lyophilizing, or precipitating out the collagen. A variety of geometrical shapes like sheets, tubes, sponges or fibers can be obtained from the collagen in this way. The resulting materials, however, do not have the mechanical strength of the naturally occurring fibrous collagen structure.

A major problem in the use of collagen-based materials, and especially whole tissue xenografts, in which the donor and recipient are phylogenetically distant, for implantation is that these materials are prone to hyperacute rejection. This is a rapid and violent rejection reaction that leads to the destruction of the xenograft. Hyperacute rejection appears to be triggered by components of natural immunity, most notably natural antibodies and complement.

In order to use collagen-based materials in manufacturing medical devices, particularly bioprosthetic implants, their durability and in vivo performance typically need to be improved. This can be done by crosslinking the material. Crosslinking of collagen-based materials is used to suppress the antigenicity of the material in order to prevent the hyperacute rejection reaction. In addition, crosslinking is used to improve mechanical properties and enhance resistance to degradation.

Crosslinking can be performed by means of physical methods, including, for example, UV irradiation and dehydrothermal crosslinking. These methods result in a direct, but generally low density crosslinking. Several chemical crosslinking methods for collagen-based materials are known. These methods involve the reaction of a bifunctional reagent with the amine groups of lysine or hydroxylysine residues on different polypeptide chains or the activation of carboxyl groups of glutamic and aspartic acid residues followed by the reaction with an amine group of another polypeptide chain to give an amide bond.

Compared with other known methods, glutaraldehyde (GA) crosslinking of collagen provides materials with the highest degree of crosslinking. It is currently the most frequently used chemical crosslinking reagent for collagen-based materials. Glutaraldehyde is a five carbon aliphatic molecule with an aldehyde at each end of the chain rendering it bifunctional. The aldehyde is able to chemically interact with amino groups on collagen to form chemical bonds. This crosslinking agent is readily available, inexpensive, and forms aqueous solutions that can effectively crosslink tissue in a relatively short period. Using GA crosslinking, increased resistance to biodegradation, reduced antigenicity, and improved mechanical properties of collagen-based materials can be achieved. Despite improved host acceptance, crosslinking of collagen-based materials using GA has shown to have cytotoxic characteristics, both in vitro and in vivo. Also, crosslinking of collagen-based materials using GA tends to result in stiffening of the material and calcification.

Crosslinking can also be accomplished with diisocyanates by bridging of amine groups on two adjacent polypeptide chains. In the first step, reaction of the isocyanate group with a (hydroxy)lysine amine group occurs, resulting in the formation of a urea bond. Thereafter a crosslink is formed by reaction of the second isocyanate group with another amine group. Diisocyanates do not show condensation reactions as observed in GA crosslinking. Also, no residual reagents are left in the material. A disadvantage, however, is the toxicity of diisocyanates and limited water solubility of most diisocyanates.

Another method of crosslinking involves the formation of an acyl azide. The acyl azide method involves the activation of carboxyl groups in the polypeptide chain. The activated groups form crosslinks by reaction with collagen amine groups of another chain. First, the carboxyl groups are esterified by reaction with an alcohol. This ester is then converted to a hydrazide by reaction with hydrazine ($H_2N$—$NH_2$). Acyl azide groups are formed by reaction with an acidic solution of sodium nitrite. At low temperatures and basic pH values, the acyl azide group reacts with a primary amine group to give amide bonds. This multi-step reaction results in good material properties; however, long reaction times (e.g., 7 days) are necessary. Alternatively, a method has recently been developed that does not need an esterification step or the use of hydrazine. In this method, a carboxyl group is converted to an acyl azide group in one single step by reaction with diphenylphosphorylazide (DPPA). This increases the reaction rate significantly; however, the reaction is carried out in an organic solvent (e.g., DMF), which is undesirable.

Also, water-soluble carbodiimides can be used to activate the free carboxyl groups of glutamic and aspartic acid moieties in collagen. Activation of the carboxyl groups with carbodiimides, such as 1-ethyl-3-(3-dimethylaminopropyl) carbodiimide.HCl (EDC), gives O-acylisourea groups. A condensation reaction by nucleophilic attack of a free amine group of a (hydroxy)lysine residue with urea as a leaving group results in formation of an amide crosslink. The O-acylisourea can also be hydrolyzed or rearranged to an N-acylurea, which is much more stable and will not react to form a crosslink. Addition of N-hydroxysuccinimide (NHS) prevents this rearrangement, however. In the presence of NHS, the O-acylisourea can be converted to an NHS activated carboxyl group, which also can react with a free amine group to form a crosslink. Addition of NHS increases the reaction rate. Also, crosslinking with EDC and NHS provides collagen material with a high degree of crosslinking; however, it also results in a material with a low tensile strength.

Thus, there still exists a need for methods of crosslinking collagen-based materials.

SUMMARY OF THE INVENTION

The present invention provides methods of making a bioprosthetic device (typically an implant or implantable device) comprising collagen-based material. The methods involve crosslinking the collagen-based material. Significantly, the methods of the present invention yield a material with a generally high degree of crosslinking and a generally high resistance towards enzymatic digestion, while the material maintains a relatively high degree of flexibility without substantial stiffening over time. This material is also preferably highly hydrophilic, which is believed to increase the biocompatibility of the material. The methods of the present invention are particularly suitable for crosslinking cardiovascular bioprostheses, such as heart valves and vascular grafts.

Accordingly, a method for making a bioprosthetic device made of collagen-based material having collagen amine groups and collagen carboxyl groups is provided. The method comprises: blocking at least a portion of the collagen amine groups with a blocking agent; activating at least a portion of the collagen carboxyl groups after blocking at least a portion of the collagen amine groups to form activated carboxyl groups; and contacting the activated collagen carboxyl groups with a polyfunctional spacer (preferably a bifunctional spacer) to crosslink the collagen-based material.

Another method of the present invention also includes a method for crosslinking collagen-based material comprising collagen amine groups and collagen carboxyl groups. The method comprises: blocking at least a portion of the collagen amine groups with a blocking agent to form blocked amine groups; contacting the collagen-based material having the blocked amine groups with a polyfunctional spacer (preferably a bifunctional spacer) for a time sufficient for the spacer to penetrate the collagen-based material; and activating at least a portion of the collagen carboxyl groups of the collagen-based material toward the polyfunctional spacer to crosslink the collagen-based material.

Preferably, the blocking agent is selected from the group of an acylating agent, an aminating agent, and a biologically active derivative thereof. If necessary for enhanced stability, the blocking step comprises reacting the collagen amine groups with an aminating agent in the presence of a reducing agent. Significantly, the method of the present invention includes blocking at least about 75% of the collagen amine groups. As used herein, the collagen amine groups are those originally present in the collagen-based material.

Preferably, the step of activating comprises contacting the free collagen carboxyl groups with an activating agent selected from the group of a carbodiimide, an azide, 1,1'-carbonyldiimidazole, N,N'-disuccinimidyl carbonate, 2-ethoxy-1-ethoxycarbonyl-1,2-dihydroquinoline, and 1,2-benzisoxazol-3-yl-diphenyl phosphate, N-ethyl-5-phenylisoxazolium-s'-sulfonate, and mixtures thereof. A particularly preferred activating agent is the partially water soluble carbodiimide, 1-ethyl-3-(3-dimethylaminopropyl) carbodiimide.HCl. To enhance the stability of the reactive intermediate, particularly when a carbodiimide is the activating agent, the step of activating preferably comprises reacting the collagen carboxyl groups with an activating agent in the presence of a stabilizing agent, such as N-hydroxysuccinimide.

The polyfunctional spacer used in the method of the present invention is preferably bifunctional and hydrophilic. A particularly preferred spacer is a hydrophilic diamine spacer. A preferred class of such spacers is selected from the group of polyethyleneglycol spacers, polypropyleneglycol spacers, polyethylene-propyleneglycol spacers, and mixtures thereof. Such spacers are preferably represented by the following general formula:

wherein: x+z=0–70 and y=0–90.

DETAILED DESCRIPTION OF THE INVENTION

Figure 1:
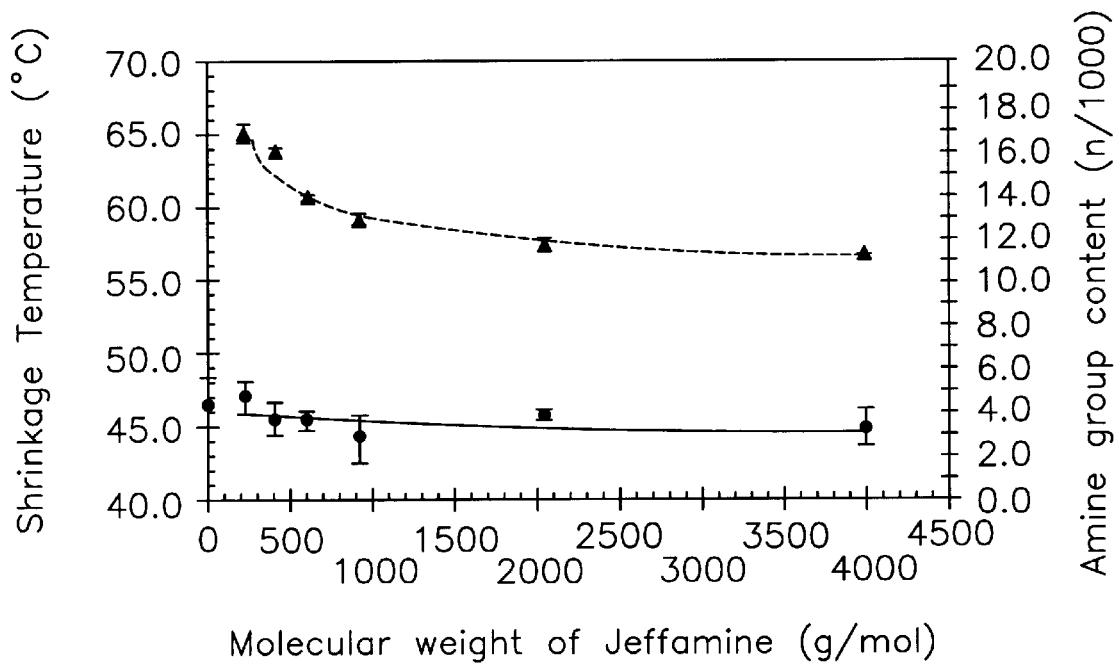
FIG. 1 Shrinkage temperature (▲) and free amine group content (●) of collagen crosslinked with EDC/NHS and JEFFAMINE spacers with different molecular weight (RT, t=24 hours; 0.25M MES, pH=5.0; molar ratio spacer:COOH=1:1; molar ratio EDC:NHS:COOH=5:2:1; reaction volume=250 ml/g).

The present invention provides a method for making a bioprosthetic device, which is derived in whole or in part from natural tissues that contain collagen-based materials. Such bioprosthetic devices include, for example, heart valves and other heart components, vascular replacements or grafts, urinary tract and bladder replacements, bowel and tissue resections, tendon replacements, and the like. Such collagen-based materials include whole tissue (i.e., tissue containing collagen and noncollagenous substances or cells), only the collagen matrix without the noncollagenous substances, and purified fibrous collagen. Typically, and preferably, however, whole tissues are used in making bioprosthetic implants.

Specifically, the present invention provides methods for making a bioprosthetic device made of collagen-based material, such as a heart valve, by crosslinking the collagen-based material with a polyfunctional spacer (preferably a bifunctional spacer). More specifically, these methods involve first blocking at least a portion (and preferably, a majority) of the free collagen amine groups with one or more blocking agents, subsequently activating at least a portion (and preferably, a majority) of the collagen carboxyl groups with one or more activating reagents, and then contacting the activated collagen carboxyl groups with one or more polyfunctional spacers (preferably bifunctional spacers) to crosslink the collagen-based material. In this way, generally only the carboxyl groups, and few if any of the amine groups, of the collagen-based material are involved in crosslinking. This provides significant advantage, as discussed in further detail below.

In the methods of the present invention the free amine groups of the collagen-based materials (often simply referred to herein as "collagen") can be blocked by various types of chemical reagents. The four major types of reactions through which blocking of free amines can be achieved are: (1) acylation reaction; (2) amination reaction, preferably involving reductive amination using aldehydes or ketones; (3) amination reaction using epoxides; and (4) amination reaction with sulphonyl or sulphonic acid derivatives. Preferably, small blocking agents, i.e., those having about two to six carbon atoms in length, are used in order to prevent significant disruption of the native triple helix structure of the collagen. Although such reactions involving the use of small blocking agents are preferred, biologically active compounds can also be used to block the free amine groups.

There are numerous acylating agents for use in blocking the amine groups using the acylation reaction. Of particular importance are the isocyanates, isothiocyanates, acid halides, acid anhydrides, activated esters (i.e., esters with a good leaving group easily released upon reaction with an amine) such as N-hydroxysuccinimide ester, and imidoesters. The ester and imidoester reagents are the most preferred. Many esters are readily available, relatively easy to prepare, and more stable, when compared to the corresponding acyl halide or anhydride.

Imidoesters are very specific towards amino groups. In mild alkaline conditions they react with amines to form imidoamines; the products carry a positive charge at physiological pH. Amidation therefore retains the net charges of the protein minimizing the effect of charge on protein conformation. Isocyanates and isothiocyanates react with amino groups, but also with sulfhydryl, imidazolyl, tyrosyl, and carboxyl groups of proteins. Although only amino groups yield stable products, these acylating agents are less specific than activated esters or imidoesters.

Preferred acylating agents include, but are not limited to: N-hydroxy succinimide esters (NHS), such as acetic acid N-hydroxysuccinimide ester, sulfo-NHS-acetate, and propionic acid N-hydroxysuccinimide ester; p-nitrophenyl esters such as p-nitrophenyl formate, p-nitrophenyl acetate, and p-nitrophenyl butyrate; 1-acetylimidazole; and citraconic anhydride (reversible blocker).

There are numerous aminating agents (e.g., alkylating agents) for use in blocking the amine groups using the amination reaction. Particularly preferred are aldehydes and ketones. Reaction of a free amine with an aldehyde or ketone yields an imine (or Schiff base) that is quite stable (particularly when an aryl group is present). If necessary, however, the formed imine can be further stabilized through reduction with reducing agents like sodium cyanoborohydride, sodium borohydride, or borane reagents such as dimethylamine borane, trimethylamine borane or morpholine borane.

Aldehydes are preferred aminating agents because ketones generally react more slowly and often require higher temperatures and longer reaction times. A wide variety of aldehydes can be used. Preferably, the aldehydes are monofunctional aldehydes to avoid undesirable crosslinking. Examples of monofunctional aldehydes include, but are not limited to, propanal, butanal, and hexanal (caproaldehyde).

When using an aminating agent, the structure formed is a secondary amine, which, theoretically, could react with activated carboxyls. It has been surprisingly discovered, however, that these secondary amine groups are sufficiently sterically hindered that, under typical reaction conditions, crosslinking does not occur.

Epoxides can be also used as the aminating agent to block the amine groups. An epoxide also forms a secondary amine; however, it is anticipated that such groups will also be sufficiently sterically hindered that, under typical reaction conditions, crosslinking will not occur. Preferably, the epoxide is a monofunctional epoxide. Suitable epoxides include, for example, iso-propylglycidylether and n-butylglycidylether. The use of an epoxide as the blocking agent is less desirable because the reaction tends to be slow and less effective.

Sulphonyl or sulphonic acid derivatives are another group of aminating agents that may be used to block free amine groups. Preferably, the sulphonyl or sulphonic acid derivative is monofunctional. An exemplary reagent is 2,4,6-trinitrobenzenesulfonic acid, for example.

A wide variety of biologically active derivatives of such compounds (i.e., those containing an appropriate reactive moiety such as an ester, aldehyde, or ketone, for example) can be used to block the free amine groups. As a result, desirable biological functions can be included into the collagenous matrix that may improve biocompatibility and overall performance. An example is aldehyde-functional heparin, obtained either through periodate oxidation (periodate-heparin) or nitrous acid degradation (NAD-heparin).

Preferably, the methods of the present invention include blocking the free amine groups using an acylation reaction or an amination reaction. Considering ease of operation and blocking efficacy, more preferably, blocking the free collagen amine groups is done through the use of activated esters like acetic acid N-hydroxysuccinimide (HAc-NHS) (for acylation) or short-chained aliphatic monofunctional aldehydes like propanal or butanal (for amination (e.g., alkylation)).

Significantly, the acylating agents are particularly preferred because they are capable of blocking a majority of the free amine groups with substantially no distortion of the collagen triple helix configuration. This is an important selection criteria for the choice of blocking agent and can be determined readily easily. Calorimetry, for instance, can be used to determine the extent to which blocking has disrupted the native triple helix configuration of the collagen. Disruption of the triple helix is denoted by a decrease of the onset of the collagen denaturation temperature.

A mixture of the above blocking agents can be used in the methods of the present invention. The blocking agent (or mixture of blocking agents) is used in an amount effective to block at least a portion, preferably, a majority (i.e., greater than about 50%), of the free amine groups. More preferably, the blocking agent(s) is used in a significant molar excess relative to the number of free amine groups.

The blocking reaction is preferably carried out in an aqueous solution, and more preferably, in a buffered aqueous solution having a pH of about 6 to about 7. The temperature of this reaction should be below that at which the collagen-based material is denatured. Thus, although increased temperatures do increase reaction rates, the reaction is preferably performed at room temperature (i.e., about 20–25° C.), and more preferably, at about 21° C.

Preferably, such blocking agents are capable of blocking at least about 75% of the free collagen amine groups, more preferably, at least about 80%, and most preferably, at least about 90%, of the free collagen amine groups. Such deactivation or blocking of the free collagen amine groups decreases the formation of zero-length crosslinks, i.e., reaction of activated carboxyl groups with free amine groups of collagen. This is advantageous because a large number of zero-length crosslinks makes collagenous materials stiff and brittle, which is in contrast to the desired mechanical properties of a bioprosthetic device.

Typically, the relatively small number of free amine groups that are not blocked are not easily accessible due to steric hindrance, and as such would not be able to participate in zero-length crosslinking. Another favorable aspect is the fact that it is believed that blocking the amine groups provides improvement in the biocompatibility of the collagen-based material because free amine groups have been suggested to be involved in the immune response.

Once the free collagen amine groups are sufficiently blocked, the free collagen carboxyl groups can be crosslinked. This is done by first activating the carboxyl groups. Preferably, this is done by initially contacting the collagen-based material with the crosslinking agent (i.e., spacer), and allowing it to penetrate into the collegen-based material, and then activating the carboxyl groups, which allows for interaction with the crosslinking agent.

The free carboxyl groups can be activated by a variety of methods. Carbodiimide reagents are well-known activating agents and traditionally most often used. Reaction between a carboxyl group and a carbodiimide yields the reactive intermediate O-acylisourea; this intermediate is prone to a nucleophilic attack in a subsequent step. In addition, an intramolecular rearrangement reaction in which the O-acylisourea rearranges to the much more stable, and much less reactive, N-acylurea may happen. Under typical reaction conditions, the half-life of the O-acylisourea is in the range of seconds to minutes.

This reactive O-acylisourea can be stabilized through the use of a succinimide or other stabilizing agents. Using a stabilizing agent in addition to the activating agent can increase the half-life of the O-acylisourea to 30–40 minutes under typical reaction conditions. Also, significantly, the intramolecular rearrangement reaction is suppressed. Typically, these stabilizing agents themselves are also capable of activating the carboxyl groups, although much less effectively than when combined with carbodiimides.

Examples of activating agents other than carbodiimide include, but are not limited to, those typically used in peptide synthesis. Examples include 1,1'-carbonyldiimidazole (CDI), N,N'-disuccinimidyl carbonate (DSC), 2-ethoxy-1-ethoxycarbonyl-1,2-dihydroquinoline (EEDQ), and 1,2-benzisoxazol-3-yl-diphenyl phosphate (BDP), and N-ethyl-5-phenylisoxazolium-s'-sulfonate (Woodwards Reagent K). Such activating agents are at least partially soluble in water. Although activating agents that are not at least partially water soluble, such as azides (e.g., diphenylphophorylazide as disclosed in U.S. Pat. No. 5,264,551 (Petite et al.)), can be used in the method of the present invention, they are not particularly desirable. Mixtures of activating agents can be used.

Preferably, the free collagen carboxyl groups are activated by contacting them with a carbodiimide that is at least partially soluble in water. A particularly preferred water-soluble carbodiimide suitable for use in the present invention is 1-ethyl-3-(3-dimethylaminopropyl) carbodiimide-.HCl (EDC). Other suitable carbodiimides include, for example, cyanamide and N,N'-dicyclohexylcarbodiimide (DCC), N,N'-diisopropylcarbodiimide (DIC), and 1-cyclohexyl-3-(2-morpholinoethyl) carbodiimide metho-p-toluenesulfonate (CMC).

As stated above, when a carbodiimide is used to activate the carboxyl groups, O-acylisourea groups are formed that can rearrange to less reactive N-acylurea groups. The addition of N-hydroxysuccinimide (NHS) is known to decrease this tendency for rearrangement. Other stabilizing agents, such as N-hydroxybenzotriazole (HOBt), N-hydroxy-5-norbornene-endo-2,3-dicarboximide (HONB), 4-dimethylaminopyridine (DMAP), and the sulfo-derivative of N-hydroxysuccinimide, are also capable of accomplishing this. Mixtures of such stabilizing agents can be used. In particularly preferred methods of the present invention, the collagen carboxyl groups are activated using a mixture of a carbodiimide (preferably, EDC) and NHS.

Various mixtures of the above activating agents and optional stabilizing agents can be used in the methods of the present invention. The activating agent or agents are used in amounts effective to activate at least a portion, and preferably, a majority (i.e., greater than about 50%), of the free collegen carboxyl groups. More preferably, the activating agent or agents are used in a molar excess relative to the number of free collagen carboxyl groups. The stabilizing agent or agents are used in an amount effective to stabilize a majority of the activated carboxyl groups. Preferably, the stabilizing agent or agents are used in an amount of at least a level that equals the number of free collagen carboxyl groups. More preferably, the stabilizing agent or agents are used in a molar excess relative to the number of free collagen carboxyl groups, but preferably not exceeding the molar level of the activating agent or agents.

The activating reaction is preferably carried out in an aqueous solution, more preferably, a buffered aqueous solution having a pH of about 4 to about 9 (preferably, about 5 to about 7, and more preferably, about 5 to about 6). The temperature of this reaction should be below that at which the collagen-based material is denatured. Thus, although increased temperatures do increase reaction rates, the reaction is preferably performed at room temperature, and more preferably, at about 21° C.

The activated carboxyl groups are then reacted with a polyfunctional spacer (preferably a bifunctional spacer) to crosslink the collagen-based material. It is believed that the introduction of spacers allows the formation of crosslinks that not only bridge the distance between two adjacent collagen fibers or fiber bundles, but also introduce extra flexibility into the whole matrix. Preferably, the bifunctional spacer is a diamine spacer, although other bifunctional spacers can be used such as diepoxides and diesters. More preferably, the bifunctional spacer is a diamine spacer of largely hydrophilic nature, soluble in aqueous solutions, with the reactive moieties preferably located at the respective ends of the longest molecular chain. The spacers may be straight-chained or branched-chained, appropriately substituted compounds. Further substitutions in the chain should not interfere with the crosslinking process and/or diminish the solubility of the spacers in aqueous solutions. Hydrophilicity of the spacer is believed to be advantageous as this can effect infiltration and diffusion of tissue fluid through the bioprosthetic matrix.

Suitable hydrophilic diamine spacers include, for example, the diamine derivatives of polyethyleneglycol and polypropyleneglycol oligomers and polymers, and polyethylene-polypropyleneglycol copolymers, such as for example O,O'-bis(3-aminopropyl)diethyleneglycol, O,O'-bis(2-aminopropyl)polypropyleneglycol, and O,O'-bis(2-aminopropyl)polyethyleneglycol. Furthermore, aliphatic diamines of about two to about eight carbon atoms in length are suitable spacers. This includes compounds with substitutions in the carbon chain, such as, for example, 1,4-diaminobutane, 1,6-diaminohexane, and 1,5-diamino-2-methylpentane. A preferred class of hydrophilic diamine spacers include polyethyleneglycol spacers, polypropyleneglycol spacers, and polyethylene-propyleneglycol spacers, which can be represented by the following general formula:

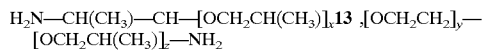

wherein: x+z=0–70 and y=0–90; preferably, x+z=0–35 and y=0–45. Such spacers are commercially available from a variety of sources, such as Aldrich Chemical Co., and Texaco Chemical Co., under the trade designation "JEFFAMINE." Such compounds are highly hydrophilic polymers having a widely varying, but well characterized, molecular weight.

The use of hydrophilic spacers can advantageously render the crosslinked material hydrophilic. As stated above, this is believed to effect proper infiltration and diffusion of tissue fluid through the bioprosthetic matrix. This provides a supply of oxygen, nutritive substances, and electrolytes into the tissue, as well as drainage of metabolized substances from the tissue. As a result, the growth of capillary blood vessels and cells will be promoted, and consequently a good healing response to the implanted material.

Additionally, it is believed that crosslinking agents having a highly flexible, long-chain structure will effect crosslinking in between adjacent fibers and fiber bundles, which will have a beneficial effect on the mechanical properties of the resultant crosslinked material.

The spacer(s) are used in amounts effective to crosslink a desired number of the activated carboxyl groups. Preferably, this amount involves a molar ratio of the bifunctional spacer(s) relative to the number of activated carboxylic groups of at least about 1:2, and more preferably of about 1:1.

The crosslinking reaction is preferably carried out in an aqueous solution, and more preferably, a buffered aqueous solution having a pH of about 4 to about 9 (preferably, about 5 to about 7, and more preferably, about 5 to about 6). The temperature of this reaction should be below that at which the collagen-based material is denatured. Thus, although increased temperatures do increase reaction rates, the reaction is preferably performed at room temperature, and more preferably, at about 21° C.

Preferably, the methods of the present invention involve initially blocking of the free collagen amine groups, contacting the collagen-based material with the spacer molecules to allow them to imbibe (i.e., penetrate) the collagen-based material, and then activating the collagen carboxyl groups toward the spacer molecules. Imbibement of the collagenous material prior to addition of the reagents that activate the carboxyl groups toward the spacer molecules significantly enhances the efficacy of the crosslinking process. This step typically is carried out in about 15 minutes. The temperature of this imbibing step should be below that at which the collagen-based material is denatured. Thus, although increased temperatures do increase the rate of imbibement, the reaction is preferably performed at room temperature, and more preferably, at about 21° C.

Crosslinking of collagen-based materials according to the methods of the present invention yield a material with a generally high degree of crosslinking and a generally high resistance toward enzymatic digestion, while the material maintains a relatively high degree of flexibility without substantial stiffening over time. This material is also preferably highly hydrophilic, which is believed to increase the biocompatibility of the material. The great reduction in free amine groups also contributes to a better biocompatibility by lowering the antigenic potential of the material. As discussed before, the biocompatibility of this material can also be improved by blocking the amine groups with appropriate biologically active molecules, such as for instance, the very blood compatible molecule heparin, instead of using small biologically non-active molecules. These properties make the method according to the present invention particularly suitable for crosslinking of cardiovascular bioprostheses, such as heart valves and vascular grafts.

The invention will be further described by reference to the following detailed examples. These examples are offered to further illustrate the various specific and illustrative embodiments and techniques. It should be understood, however, that many variations and modifications may be made while remaining within the scope of the present invention.

Experimental Examples

Materials and Methods

Preparation of DSC. Dermal sheep collagen (DSC) was used as a model for porcine aortic heart valves because this material provides a tissue matrix-like structure, while being a pure collagen material. The latter allows for more precise evaluation and characterization of the material after having the crosslinking process employed, and as such a better understanding of the relationship between the crosslinking chemistry and consequent material behavior, mechanically as well as biologically, is obtained. The material was obtained from the Zuid-Nederlandse Zeemlederfabriek (Oosterhout, The Netherlands). DSC was prepared in a process in which the skin first was depilated and immersed in a lime-sodium sulfide solution to remove the epidermis. Non-collagenous substances were removed using proteolytic enzymes whereafter the skin was split to obtain the dermal layer. The remaining fibrous collagen network was extensively washed with water (4 times), with acetone (2 times), and with deionized water (2 times) before freeze-drying. This procedure yielded non-crosslinked DSC (NDSC).

Blocking of free amine groups-acylation process. The acylating agent acetic acid N-hydroxysuccinimide ester (HAc-NHS; Sigma, Zwijndrecht, The Netherlands) was used to block the free amine groups of collagen to prevent subsequent reaction of the activated carboxyl groups with these amine groups. A sheet of 1 gram (g) of NDSC was immersed in 20 milliliters (ml) of a 0.25Molar (M) 2-(N-morpholino)ethanesulfonic acid (MES) (Fluka, Buchs, Switzerland) buffered solution (pH=6.5) containing 0.55 g HAc-NHS; molar ratio of HAc-NHS to free amine groups of collagen was approximately 10:1. The reaction was allowed to proceed for 6 hours, while every 2 hours an additional amount of 0.11 g HAc-NHS was added. After reaction the DSC was washed 4 times with deionized water and freeze-dried. This procedure yielded HAc-NHS blocked DSC (HBDSC).

Blocking of free amine groups-reductive amination process. Butanal (or butyraldehyde), a monofunctional aldehyde-reagent, was used to block the free amine groups of collagen to prevent subsequent reaction of the activated carboxyl groups with these amine groups. Sodium cyanoborohydride ($NaCNBH_3$) was used for reductive stabilization of the Schiff-base formed after reaction of butanal with the collagen free amine group. A sheet of 1 g of NDSC was immersed in 50 ml of a 0.25M MES buffer solution (pH=6.5) containing 3.9 ml butyraldehyde (p.a.; Acros, Geel, Belgium) and 1 mg/ml $NaCNBH_3$ (Aldrich, Zwijndrecht, The Netherlands) for 6 hours, while every 2 hours an additional amount of 1 mg/ml $NaCNBH_3$ was added. The molar ratio of butanal to free amine groups of collagen was approximately 125:1. After reaction the DSC was washed 4 times with deionized water and freeze-dried. This procedure yielded butanal blocked DSC (BBDSC).

Crosslinking with EDC, NHS, and "JEFFAMINE" spacers. Samples of HAc-NHS blocked DSC (HBDSC) weighing 1 g were immersed in a 0.25M MES buffered solution (pH=5.0) containing 1.15 g 1-ethyl-3-(3-dimethylaminopropyl)carbodiimide.HCl (EDC; Aldrich, Zwijndrecht, The Netherlands), 0.276 g N-hydroxysuccinimide (NHS; Aldrich, Zwijndrecht, The Netherlands) and the desired amount of JEFFAMINE. Two types of JEFFAMINE's were used; poly(propyleneglycol) bis(2-aminopropylether) (JEFFAMINE D) and poly (propyleneglycol-b-ethyleneglycol-b -propyleneglycol)bis (2-aminopropylether) (JEFFAMINE ED). The molar ratio of EDC to NHS to free collagen COOH groups was 5:2:1 and kept constant throughout all experiments. In four experiments the influence of the average molecular weight of the spacer, the molar ratio of the spacer to free collagen COOH groups, the time of reaction and the concentration of the reagents on the degree of crosslinking was investigated.

In the first experiment spacer molecules with various average molecular weights (Mn) were used; JEFFAMINE D230, JEFFAMINE D400 (both from Aldrich, Bornem, Belgium); JEFFAMINE ED600, JEFFAMINE ED900, JEFFAMINE ED2001, and JEFFAMINE ED4000 (all from Texaco Chemical Company, Bellaire, Tex., USA) with a Mn of 230 g/mole, 400 g/mole, 600 g/mole, 900 g/mole, 2000 g/mole, and 4000 g/mole, respectively. Also, one sample was immersed in a solution containing only EDC and NHS. The time of reaction was 24 hours, the reaction volume was 250 ml, and the molar ratio of spacer to collagen COOH was set at 1:1.

In the second experiment, molar ratios of spacer to collagen COOH of 1:1, 2:1, 3:1, 4:1, 5:1, 6:1, and 10:1 were used. The time of reaction was 24 hours, the reaction volume was 500 ml and the JEFFAMINE D230 spacer was used.

In the third experiment, the time of reaction was varied between 1 hour and 96 hours. The reaction volume was 500 ml and the JEFFAMINE D230 spacer was used in a molar ratio of spacer to collagen COOH groups of 1:1.

In the fourth experiment, the concentration of the reagents was varied by varying the total reaction volume between 10 ml/g collagen and 500 ml/g collagen. The JEFFAMINE D230 spacer was used, with the molar ratio of spacer to collagen COOH was kept constant at 1:1, and the time of reaction was set at 150 minutes. In this experiment, the concentration of buffer was raised to 1M MES to maintain a good buffering capacity in the more concentrated solutions.

In all experiments, after the crosslinking reaction, the samples were successively washed for 2 hours in a 0.1M $Na_2HPO_4$ solution, washed 3 times in deionized water, and freeze-dried.

The study on the effect of molar ratio of spacer to collagen COOH groups was further extended, by doing an additional experiment in which the molar ratios of spacer to collagen COOH of 1:4, 1:2, 1:1, and 2:1 were used. The reaction was performed for 150 minutes in a 1M MES buffer (pH=5.0); the reaction volume was 20 ml/g collagen. The molar ratio of EDC:NHS:collagen COOH as before was kept at 5:2:1.

The study on the effect of reaction time was repeated partially, i.e., between 1 hour and 4 hours, to more precisely characterize the course of the reaction. The reaction was performed in a 1M MES buffer (pH=5.0); the reaction volume was 20 ml/g collagen. The molar ratio of EDC:NHS:collagen COOH as before was kept at 5:2:1, while the molar ratio of spacer to collagen COOH was set at 1:1.

The effect of solution pH was also investigated. Crosslinking reactions were performed for 150 minutes in a 1M MES buffer, pH varying between 5 and 7; the reaction volume was 20 ml/g collagen. The molar ratio of EDC:NHS:collagen COOH as before was kept at 5:2:1, while the molar ratio of spacer to collagen COOH was set at 1:1.

Free amine group content. The primary amine group content of treated and non-treated DSC samples, expressed as the number of free amine groups present per 1000 amino acids (n/1000), was determined using a 2,4,6-trinitrobenzenesulfonic acid (TNBS; 1.0M solution in water, Fluka, Buchs, Switzerland) calorimetric assay. To a sample of 5–15 milligrams (mg) of DSC subsequently 5 ml of a 4% (weight/volume) aqueous $NaHCO_3$ (Aldrich, Bornem, Belgium) solution and 5 ml of a freshly prepared 0.5% (weight/volume) aqueous TNBS solution was added. After reaction for 2 hours at 40° C., 25 ml of 6M HCl (Merck, Darmstadt, Germany) was added and the temperature was raised to 60° C. When complete solubilization of DSC was achieved (approximately 90 minutes after addition of HCl) the resulting solution was diluted with 15 ml of deionized water and the absorbance was measured on a Hewlett-Packard HP8452A UV/VIS spectrophotometer at a wavelength of 345 nm. A control was prepared applying the same procedure except that a sample of DSC was added after the addition of HCl. The free amine group content was calculated using a molar absorption coefficient of 14600 $l \cdot mol^{-1}$ cm$^{-1}$ for trinitrophenyl lysine [Wang C. L., et al., *Biochim. Biophys. Acta*, 544, 555–567, (1978)].

Degree of crosslinking Differential scanning calorimetry was used to study the efficacy of the various crosslinking procedures. Heating (crosslinked) collagen will induce a structural transition of the native triple helical structure at a certain temperature dependent on the nature and degree of crosslinking. Introduction of covalent crosslinks will increase the stability of the triple helix, thus increasing the denaturation temperature. The temperature at which denaturation takes place is also often referred to as shrinkage temperature ($T_s$), as shrinkage is the macroscopic manifestation of the transformation of the native triple helix structure to the random coil configuration.

Treated and non-treated collagen samples were characterized using a Perkin Elmer DSC7 series. In a typical run 5–8 milligrams (mg) collagen was placed into a 50 microliter ($\mu$l) aluminum sample pan (2 bar maximum internal pressure), after which 5 $\mu$l/mg 0.1M phosphate buffer (pH=6.88; 0.05M Na$_2$HPO$_4$, 0.05M NaH$_2$PO$_4$—both Merck, Darmstadt, Germany) was added to hydrate the collagen. The sample pan was covered with an appropriate cover and the whole was crimp pressed. An empty sample pan was used as the reference. Typically, a run was started at 20° C. (load temperature); after 2 minutes, samples were heated to 100° C., applying a heating rate of 2° C./minute. Device software was used to optimize data collection, and to calculate typical properties.

Pronase digestion assay. The digestion of treated and non-treated DSC was performed by immersing a collagen disc of 10 mm diameter in 5 ml of a pre-warmed (T=37° C.) solution of 0.1M TRIS-HCl (Aldrich, Bornem, Belgium), pH=7.4, containing 5 mM CaCl$_2$ (Janssen Chimica, Geel, Belgium), 0.05 mg/ml NaN$_3$ (Merck, Darmstadt, Germany) and 25 U/ml pronase (from Streptomyces griscus, 7000 U/g, Boehringer Mannheim GmbH, Germany). The absolute amount of pronase was approximately 4.5 U/mg collagen. Degradation was discontinued at the desired time interval by the addition of 0.5 ml 0.25M EDTA (Janssen Chimica, Geel, Belgium). After homogenization for 5 minutes, the disc was washed 3 times for 5 minutes in 0.1M tris(hydroxymethyl) aminomethane hydrochloride (TRIS-HCl, pH=7.4), 3 times for 5 minutes in deionized water, and freeze-dried. The percent remaining weight was determined gravimetrically and used as a measure for the resistance towards enzymatic digestion.

Water absorption experiments. Treated and non-treated collagen discs (12 mm diameter) were placed on a water surface. The time before these samples were completely wetted was measured. Thereafter, the wet samples were blotted on lint-free tissue paper. The wet weight of the samples was measured after which the the ratio of wet weight to dry weight was calculated.

Evaluation of in vitro cytotoxicity. Collagen samples crosslinked according to the procedure disclosed herein were evaluated in an in vitro cytoxicity test. The samples were routinely sterilized by ethylene oxide (ETO). The cytotoxicity was determined according to the method of Van Luyn M. J. A., et al., *Mater. Med.*, 2, 142–248 (1991). In short, this method involves a 7 days exposure of the test material (8 mm discs) to a methylcellulose culture of human fibroblasts. This test method has been reported to be more sensitive than the established test methods, i.e., agar-overlay test and filter diffusion test.

Subcutaneous rat implants. NIH guidelines for the care and use of laboratory animals (NIH Publication #85-23 Rev. 1985) were observed. Subcutaneous implants were done in male Albino Oxford rats (AO; bred at Rijksuniversiteit Groningen, The Netherlands) of approximately 3 months of age. A subcutaneous pocket was created parallel to the spine after which ETO-sterilized 8 millimeter (mm) discs of treated collagens were implanted. At days 1, 2, 5, and 10, and weeks 3 and 6, the collagen discs with their surrounding tissue response were excised and evaluated for the cellular response, level of calcification, and the matrix degradation and/or substitution.

All explanted specimens were immersion-fixed in 2% (volume/volume) glutaraldehyde in phosphate buffered saline (PBS, pH=7.4) during at least 24 hours at 4° C.; subsequently, specimen were dehydrated in graded alcohols and embedded in EPON 812. Prior to light microscopy (LM) evaluation semithin sections (1 $\mu$m) were prepared and typically stained with Toluidine Blue stain to evaluate the cellular response and with von Kossa stain to determine levels of calcification.

Crosslinking of porcine aortic valves. Fresh porcine aortic heart valves were selected and dissected at the slaughterhouse (Premium Fleisch Emsland, Lingen, Germany). Residual fat and myocardium were removed from the valve as much as possible. After harvesting, aortic roots (leaflets and a small piece of the aorta) were rinsed four times with an ice-cold saline solution (0.9 weight percent NaCl), and stored at 4° C. in 10 mM HEPES for one night.

The following crosslinking methods were used:

(1) GA crosslinking was performed by immersing a valve in 100 ml of a 10 mM HEPES buffered solution (pH=7.4) containing 0.2 weight percent (wt-%) glutaraldehyde for 24 hours at room temperature. After crosslinking the valve was rinsed five times for 30 minutes each in saline, after which the valve was stored in 0.2 wt-% glutaraldehyde.

(2) EDC/NHS control crosslinking was performed by immersing a valve in 100 ml of a 0.05 M MES buffered solution (pH=5.5) containing 1.15 g EDC and 0.14 g NHS (molar ratio EDC:NHS:COOH(collagen)=5:1:1) assuming that one valve contains about 1 g of collagen. Crosslinking was performed at room temperature for 24 hours. After crosslinking the valve was rinsed five times for 30 minutes each in saline, and stored in 10 mM HEPES containing 20 wt-% IPA (pH=7.4).

(3) HAc-NHS/JEFFAMINE D230 crosslinking was performed by immersing a valve in 100 ml of a 0.25 M MES buffer (pH=6.5) to which 2.75 g of HAc-NHS was added. The blocking reaction was allowed to proceed for 6 hours, while after 2 hours and 4 hours an additional 0.55 g of HAc-NHS was added. Thereafter the valve was rinsed in saline three times for 15 minutes each. Following the saline rinse, the valve was imbibed with the spacer by immersing the valve in 100 ml of a 0.25 M MES buffer (pH=5.0) containing 1.38 g Jeffamine D230. After 30 minutes the valve was removed and immersed in 100 ml of a 0.25 M MES buffer (pH=5.0) containing 1.38 g JEFFAMINE D230, 5.75 g EDC, and 1.38 g NHS. The crosslinking reaction was allowed to proceed for 14 hours. Thereafter the valve was rinsed five times for 30 minutes each in saline, after which the valve was stored in 10 mM HEPES containing 20 wt-% IPA (pH=7.4).

(4) Butanal/JEFFAMINE D230 crosslinking was performed by immersing a valve in 100 ml of a 0.25 M MES buffer (pH=6.5) to which 8 ml of butanal and 100 mg of NaCNBH$_3$ were added. The blocking reaction was allowed to proceed for 6 hours, while after 2 hours and 4 hours an additional 100 mg of NaCNBH$_3$ was added. Thereafter the valve was rinsed in saline three times for 15 minutes each. Following the saline rinse, the valve was imbibed with the spacer by immersing the valve in 100 ml of a 0.25 M MES buffer (pH=5.0) containing 1.38 g JEFFAMINE D230. After 30 minutes the valve was removed and immersed in 100 ml of a 0.25M MES buffer (pH=5.0) containing 1.38 g JEFFAMINE D230, 5.75 g EDC, and 1.38 g NHS. The crosslinking reaction was allowed to proceed for 14 hours. Thereafter the valve was rinsed five times for 30 minutes each in saline, after which the valve was stored in 10 mM HEPES containing 20 wt-% IPA (pH=7.4).

(5) HAc-NHS/JEFFAMINE ED2001 crosslinking was performed by immersing a valve in 100 ml of a 0.25 M MES buffer (pH=6.5) to which 2.75 g of HAc-NHS was added. The blocking reaction was allowed to proceed for 6 hours, while after 2 hours and 4 hours an additional 0.55 g of HAc-NHS was added. Thereafter the valve was rinsed in saline three times for 15 minutes each. Following the saline rinse, the valve was imbibed with the spacer by immersing the valve in 100 ml of a 0.25M MES buffer (pH=5.0) containing 12 g JEFFAMINE ED2001. After 30 minutes the valve was removed and immersed in 100 ml of a 0.25 M MES buffer (pH=5.0) containing 12 g JEFFAMINE ED2001, 5.75 g EDC, and 1.38 g NHS. The crosslinking reaction was allowed to proceed for 14 hours. Thereafter the valve was rinsed five times for 30 minutes each in saline, after which the valve was stored in 10 mM HEPES containing 20 wt-% IPA (pH=7.4).

(6) Butanal/Jeffamine ED2001 crosslinking was performed by immersing a valve in 100 ml of a 0.25 M MES buffer (pH=6.5) to which 8 ml of butanal and 100 mg of $NaCNBH_3$ were added. The blocking reaction was allowed to proceed for 6 hours, while after 2 hours and 4 hours an additional 100 mg of $NaCNBH_3$ was added. Thereafter the valve was rinsed in saline three times for 15 minutes each. Following the saline rinse, the valve was imbibed with the spacer by immersing the valve in 100 ml of a 0.25 M MES buffer (pH=5.0) containing 12 g JEFFAMINE ED2001. After 30 minutes the valve was removed and immersed in 100 ml of a 0.25 M MES buffer (pH=5.0) containing 12 g JEFFAMINE ED2001, 5.75 g EDC, and 1.38 g NHS. The crosslinking reaction was allowed to proceed for 14 hours. Thereafter the valve was rinsed five times 30 minutes in saline, after which the valve was stored in 10 mM HEPES containing 20 wt-% IPA (pH=7.4).

Implant protocol. Three 8 mm discs of both the leaflets and the aortic wall from each of the treated porcine valves were washed three times in saline and implanted subdermally in the back (2 implants per animal) of 3 week-old male Sprague Dawley rats. All samples were retrieved after 8 weeks. The surrounding tissue capsule was removed; explant specimen were cut in half, after which one half was used for histochemical staining and the other half was lyophilized for subsequent calcium analysis.

Calcium analysis. The lyophilized samples were weighed, after which they were hydrolyzed in 6 N HCl at 85° C. for 24 hours at atmospheric pressure. Calcium levels in solution were determined by the Inductively Coupled Plasma (ICP) Atomic Emission Spectroscopy (AES) using a Perkin-Elmer Sciex Elan 500 at DSM Research, Geleen, The Netherlands. At low calcium levels, analyses were repeated, but using Mass Spectrometry (MS) for determination of calcium levels in solution. The results are expressed as milligrams of calcium per gram of dry tissue.

Results and Discussion

The method of the present invention includes the following basic steps: 1) blocking free amine groups; 2) imbibement with diamine spacer; 3) carbodiimide activation of carboxyl groups; and 4) crosslinking with diamine spacer.

Blocking of free amine groups. The first step in the crosslinking process is the blocking of the free ε-amine groups of the amino acids lysine and hydroxylysine. The main reason is to prevent further participation in the subsequent crosslinking steps. Without blocking these amine groups, carbodiimide activation of the carboxyl groups mainly will provoke the so-called zero-length crosslinking, i.e., the direct coupling of a carboxyl group to a amine group. It is known that a large number of these crosslinks makes collagenous materials stiff and brittle. Also, it has been suggested in U.S. Pat. No. 5,475,052 (Rhee et al.) that blocking free amine groups improves the immunogenicity of collagen-derived materials.

Acylation process. The collagen amine groups were blocked using NHS activated acetic acid ester through an acylation reaction. The reaction mechanism is displayed in Scheme 1.

Scheme 1

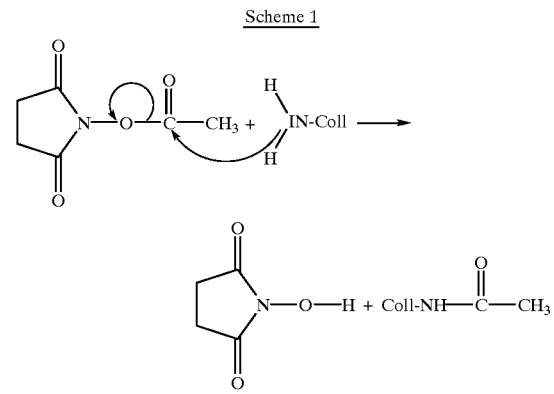

With this reagent an approximate 90% efficiency was found, accompanied by a small decrease in denaturation temperature of the base material [see Table 1]. This decrease most likely is caused by a local disruption of the triple helix structure of the collagen molecules. It is safe to assume that the few amine groups that were not blocked are not easily accessible due to steric hindrance.

TABLE 1

Effect of amine group blocking on the free amine group content and $T_s$

| material | free amine group content (n/1000) | $T_s$ (° C.) |
|---|---|---|
| NDSC | 27.9 ± 1.4 | 45.7 ± 0.1 |
| HBDSC | 2.9 ± 1.3 | 45.1 ± 0.2 |

Reductive amination process. The free amine groups were alternatively blocked using the monofunctional aldehyde butanal under reductive conditions. The reaction mechanism is displayed in Scheme 2.

Scheme 2

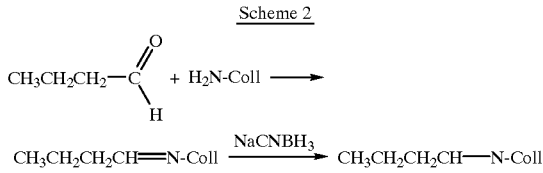

This reaction was more effective than the previous one, having an approximate 95% efficiency; it also did not dramatically change the denaturation temperature.

TABLE 2

Effect of amine group blocking on the free amine group content and $T_s$

| material | free amine group content (n/1000) | $T_s$ (° C.) |
|---|---|---|
| NDSC | 32.3 ± 0.7 | 45.3 ± 0.8 |
| BBDSC | 1.8 ± 0.2 | 44.8 ± 1.5 |

As shown in the reaction mechanism, the reaction of butanal with a free amine group yields a secondary amine that in principle is capable of reacting with an activated carboxyl group. However, these butanal-blocked amines did not participate in further cross linking, perhaps because of steric hindrance.

Although butanal is an aldehyde-functional compound, it should not be compared to glutaraldehyde, as, unlike glutaraldehyde, this compound is not capable of forming a polymeric network. Thus, after reaction, excess reagent is easily washed out and will not be any threat to the biocompatibility of the collagen-derived material.

Imbibement with diamine spacer. After blocking of the free amine groups the next step in the process is preferably the imbibement of the collagenous material with the spacer molecules. Imbibement of the collagenous material prior to addition of the reagents that activate the carboxyl groups toward the spacer molecules to crosslink the collagen-based material significantly enhances the efficacy of the crosslinking process. Although the inventors do not wish to be limited by theory, it is believed that this can be explained by the fact that in a dense material like collagen, the reaction rate is largely diffusion-dependent. By allowing the spacer molecules to penetrate the matrix before reaction is initiated, part of the diffusion limitation is overcome.

A preferred spacer-molecule is the diamino functional derivative of a poly(propyleneglycol)/poly(ethyleneglycol) polymer, such as that commercially available under the tradename JEFFAMINE. This spacer is advantageous because of its high intrinsic hydrophilicity and flexibility. The highly flexible nature of these spacer-molecules is thought to enhance the mechanical properties of the crosslinked material. The hydrophilic nature of these reagents is thought to be beneficial with respect to penetration into the dense collagenous matrix. It is also hypothesized that the use of these types of spacer-molecules will render the crosslinked material highly hydrophilic. This should effect good infiltration and diffusion of tissue fluid through the material matrix, providing supply of oxygen, nutritive substances, electrolytes and drainage of metabolites. Also, it is believed that the in-growth of capillary blood vessels and cells will be promoted, and consequently the healing response will be improved.

The diameter of the triple helix of collagen is approximately 15 Angstrom and the total diameter of a microfibril, typically comprising 5 collagen molecules laying next to each other, is approximately 40 Angstrom. In turn, fibrils composed of a number of microfibrils have a diameter of about 500 Angstrom. The calculated molecular lengths of JEFFAMINE spacers of varying average molecular weights are as follows: 230 grams/mole, 13 Angstroms; 400 grams/mole, 24 Angstroms; 600 grams/mole, 37 Angstroms; 900 grams/mole, 55 Angstroms; 2000 grams/mole, 123 Angstroms; and 4000 grams/mole, 248 Angstroms.

Taking these dimensions into account, this means that for instance the JEFFAMINE 230 only can form intramolecular crosslinks or crosslinks inside a microfibril, while longer molecules also can form crosslinks between different microfibrils. On the contrary, it is very doubtful that the high molecular weight JEFFAMINE spacers, such as JEFFAMINE 2000 or more, can form intramolecular crosslinks.

Carbodiimide activation of carboxyl groups. Crosslinking of collagen materials using carboxyl group activation has gained an increased interest in the last 5–10 years. For example, carbodiimide activated crosslinking of collagen has been described (Olde Damink L. H. H., thesis, University of Twente, Enschede, The Netherlands, 1993), as has been acyl azide crosslinking (U.S. Pat. No. 4,958,008 (Petite et al.) and U.S. Pat. No. 5,264,551 (Petite et al.)).

The water-soluble carbodiimide compound EDC activates carboxyls, and the addition of NHS increases the efficacy of the activation reaction even more. See Scheme 3. NHS not only suppresses the formation of the by-product N-acylurea, that is formed after intramolecular rearrangement of compound (1), upon reaction with compound (1) it also forms a much more stable activated carboxyl ester. Whereas the halflife $t_{1/2}$ of compound (1) is in the range of seconds to minutes, the $t_{1/2}$ of compound (2) is increased to 30–40 minutes under the reaction conditions typically employed in the currently disclosed crosslinking process.

Scheme 3
EDC/NHS activation of carboxyl groups

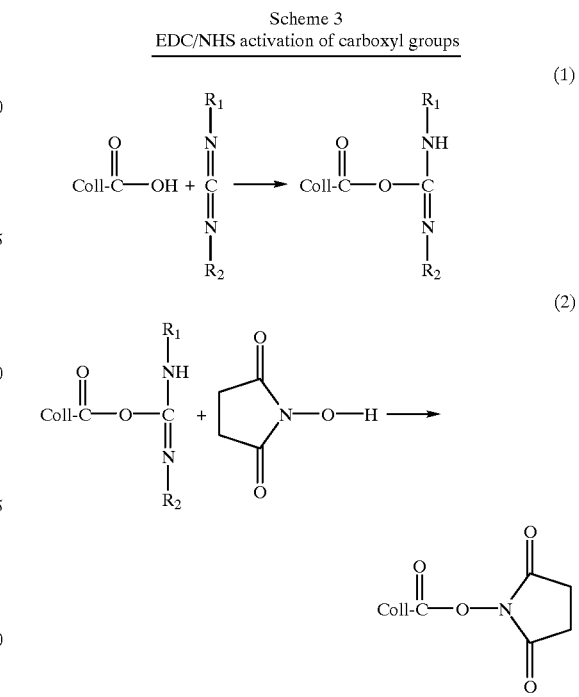

EDC = 1-ethyl-3-(3-dimethylaminopropyl)carbodiimide·HCl
NHS = N-hydroxysuccinimide Crosslinking with diamine spacer. Since the ε-amine groups of lysine and hydroxylysine have been blocked, zero-length crosslinking, i.e., the direct reaction between carboxyl groups of aspartic acid and glutamic acid and those free amines, is prevented. See scheme 4. After blocking, crosslinking occurs through reaction of both amine groups of the spacer with the activated (*) carboxyl groups. When the diamine spacer reacts only on one side, pendant amine groups are introduced into the collagen. The higher the number of pendant amine groups, the less effective crosslinking is performed. Determination of the number of the free amine group content before and after crosslinking provides the number of spacer molecules which have reacted on one side, and thus is a measure for the crosslinking efficiency.

FAMINE D230 is very low and indicates that either only a few spacer molecules reacted, or that the material is very effectively crosslinked. Because crosslinking with JEFFAMINE D230 gave the largest increase in shrinkage temperature this spacer compound is used in most of the following experiments.

Figure 2:
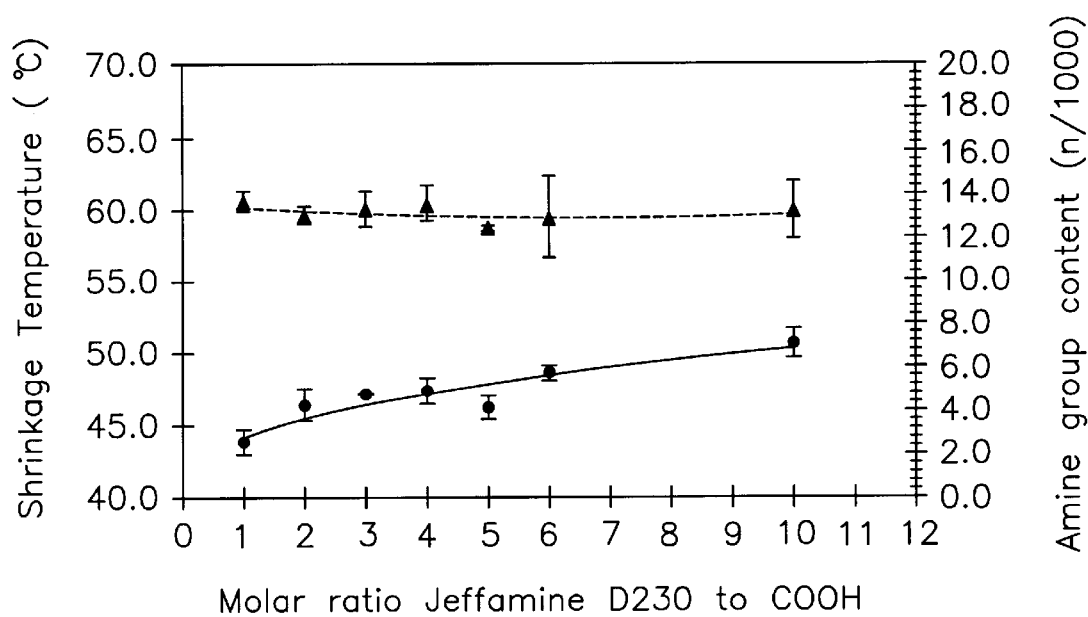
FIG. 2 Shrinkage temperature (▲) and free amine group content (●) of collagen crosslinked with EDC/NHS and JEFFAMINE D230 as a function of the molar ratio spacer::COOH (RT, t=24 hours; 0.25M MES, pH=5.0; molar ratio EDC:NHS:COOH=5:2:1; reaction volume=500 ml/g).

The influence of the molar ratio of the JEFFAMINE spacer to the number of carboxyl groups is shown in FIG. 2. Increasing the molar ratio had no profound effect on the shrinkage temperature, although it did increase masking reactions, i.e., the one-sided coupling of spacer molecules as observed by an increase in free amine group content. A molar ratio of 1:1 means that there are 2 amine groups

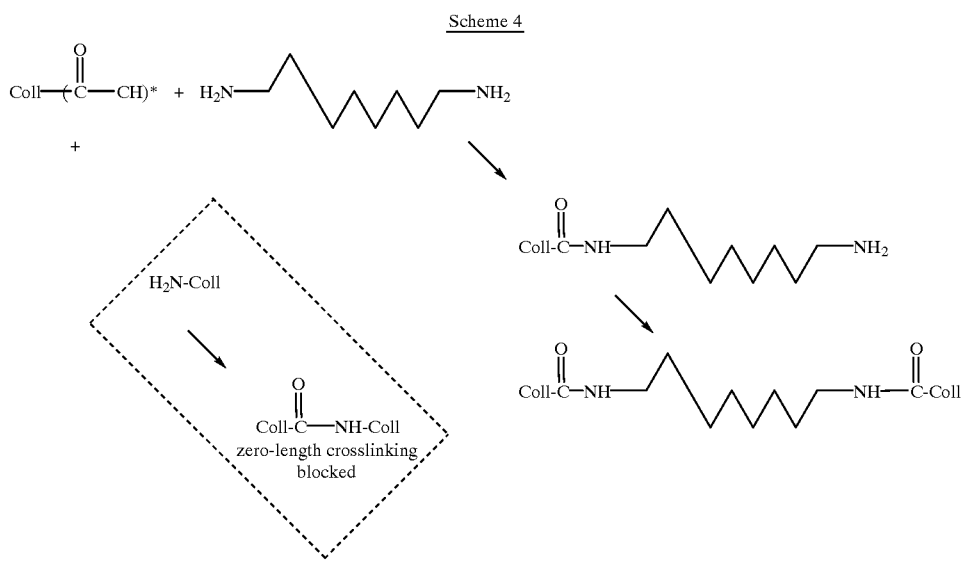

Scheme 4

The influence of the molecular weight of the spacer molecules on shrinkage temperature and amine group content was investigated. It was found that collagen crosslinked with the JEFFAMINE D230, the JEFFAMINE compound with the lowest molecular weight, demonstrated the largest increase in shrinkage temperature, whereas with increasing molecular weight the increase in shrinkage temperature was lower [FIG. 1]. It is believed that the high molecular weight spacers have more difficulty penetrating the collagenous matrix due to their size. EDC/NHS crosslinking in the absence of any JEFFAMINE compound still induces an increase in shrinkage temperature, despite having 90% of the free amine groups blocked. Because it can be expected that the most readily attainable amine groups were blocked, this observation possibly can be explained by a reaction of activated carboxyl groups with available hydroxyl groups forming ester-type linkages or even other carboxyl groups forming carboxyl anhydrides.

Collagen crosslinked with JEFFAMINE D230 also shows the highest free amine group content. The free carboxyl group content of collagen is approximately 120/1000 amino acids. This means that in theory formation of 60 crosslinks per 1000 amino acids is possible; due to steric hindrance and because some carboxyl groups are too distant from others, such a high crosslinking degree will, however, never occur. If the material is crosslinked less effectively, the number of pendant spacer molecules and also the number of free amine groups will increase. The observed increase of 2 amine groups per 1000 amino acids after crosslinking with JEFpresent per carboxyl group. A decrease of the JEFFAMINE:COOH ratio to 1:2, i.e., 1 amine per carboxyl, did not effect the shrinkage temperature nor did it effect any significant decrease of the free amine group content.

Figure 3:
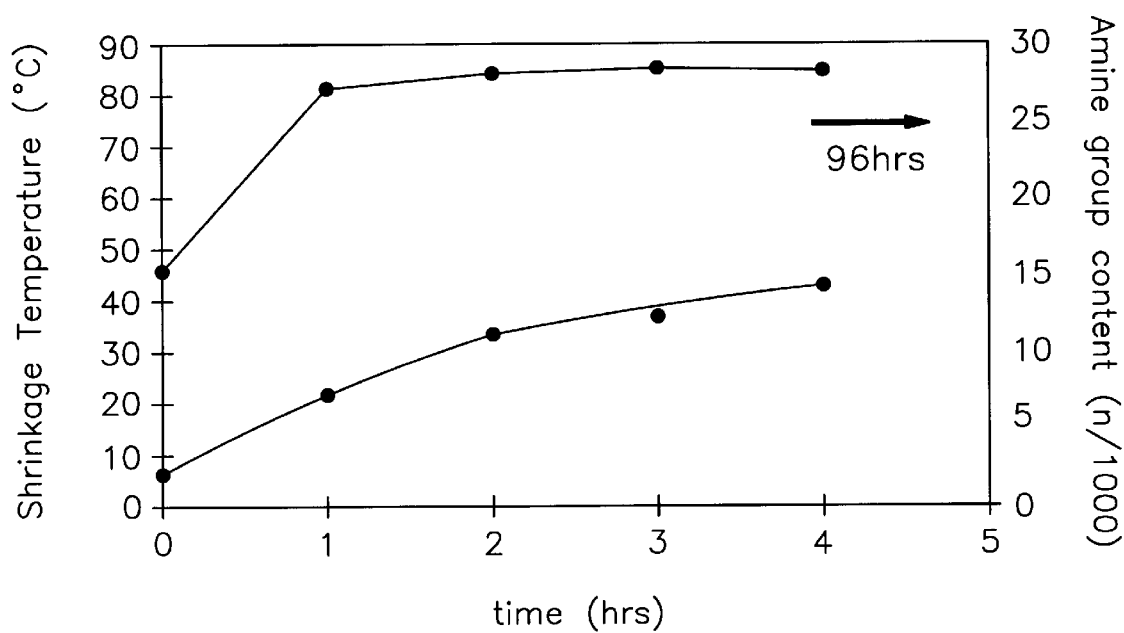
FIG. 3 Shrinkage temperature (▲) and free amine group content (●) of collagen crosslinked with EDC/NHS and JEFFAMINE D230 as a function of the reaction time (RT; 0.25M MES, pH=5.0; molar ratio spacer:COOH=1:1; molar ratio EDC:NHS:COOH=5:2:1; reaction volume=20 ml/g).

Carbodiimide activated crosslinking is a fast reaction. FIG. 3 shows that crosslinking largely was performed within 1.5–2 hours. Longer reaction times only caused more pendant groups to be built in. With increasing density of collagenous materials, however, longer reaction times may be desirable in order to achieve a homogenous distribution of crosslinks throughout the material.

Figure 4:
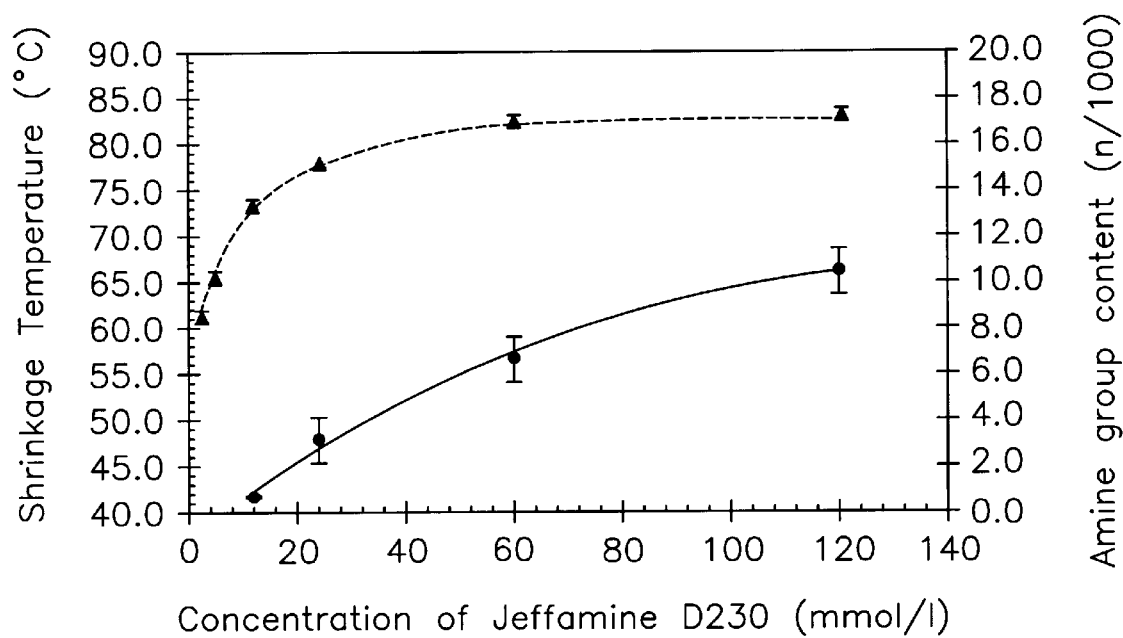
FIG. 4 Shrinkage temperature (▲) and free amine group content (●) of collagen crosslinked with EDC/NHS and JEFFAMINE D230 as a function of the concentration of JEFFAMINE D230 (RT, t=2½ hours; 0.25M MES, pH=5.0; molar ratio spacer:COOH=1:1; EDC:NHS:COOH=5:2:1).

The reaction rate during crosslinking of collagen-derived materials is highly diffusion-dependent. Besides the macroscopic event of reagent diffusion into the three-dimensional structure of the collagenous material, there is a microscopic event comprising diffusion of the appropriate reagents towards the surface of a collagen molecule in order to achieve the covalent binding of the spacer compound. This means that with increasing the bulk concentration of reagents, the efficacy of the crosslinking reaction should be increased. FIG. 4 confirms this. The increase in bulk concentration of JEFFAMINE spacer, EDC, and NHS (while maintaining molar ratios constant) showed a dramatic effect on the shrinkage temperature achieved. The large increase in free amine group content also confirms that a larger number of reactions take place. It also demonstrates that at too high concentrations the crosslinking reaction gets very inefficient.

Pronase digestion assay. One technique, traditionally used in the characterization of a crosslinking process, is the enzymatic digestion assay. Enzymatic digestion has no definite correlation with the stability of the material in the bodily environment, but it provides a good comparison of different crosslinking techniques in vitro.

In addition, through usage of different types of enzymes, the localization of crosslinks can be determined. Pronase for instance, preferentially attacks the non-helical telopeptide regions of the collagen molecule; on the contrary, collagenase attacks the triple helix itself. Differences in resistance to a certain enzyme thus may help in localizing crosslinks formed.

Figure 5:
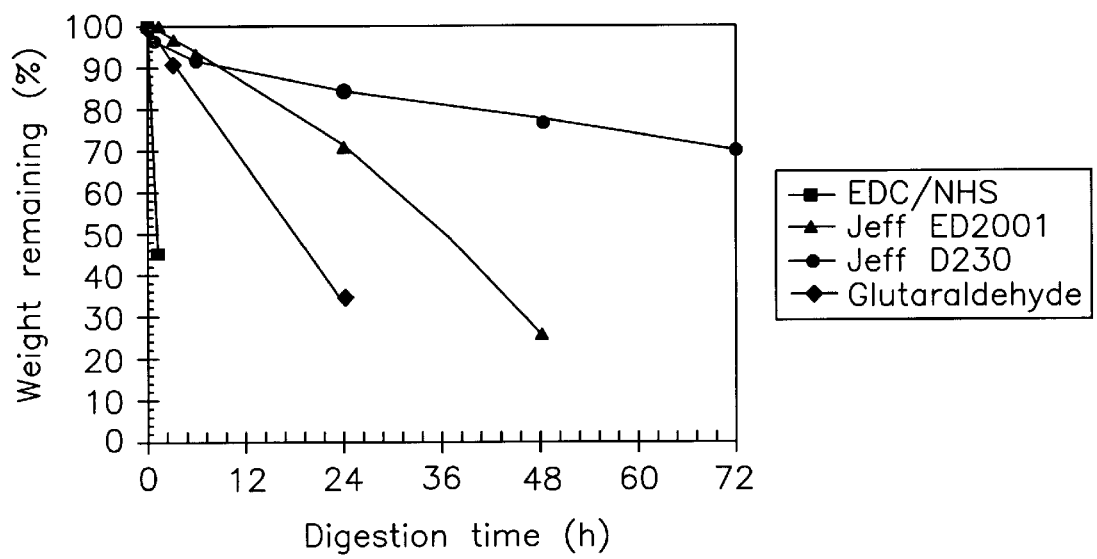
FIG. 5 Pronase digestion of various collagen discs (d=10 mm) differently crosslinked after blocking; non-crosslinked and blocked collagen were digested within 1 hour (0.1M TRIS-HCl (pH=7.4), 5 mM $CaCl_2$, 0.05 mg/ml $NaN_3$, 25 U/ml pronase; 37° C.; pronase activity=4.5 U/mg).

The results of the pronase digestion tests are presented in FIG. 5. Note that EDC/NHS, Jeff ED2001, and Jeff D230 stand for HBDSC crosslinked with this type of crosslinker, and that glutaraldehyde stands for NDSC crosslinked with glutaraldehyde. Table 3, below, shows the shrinkage temperatures of collagen crosslinked according to these various crosslinking procedures.

TABLE 3

Shrinkage temperature of samples enrolled in pronase digestion assay.

| material type | shrinkage temperature (° C.) |
| --- | --- |
| non-crosslinked – NDSC | 45.7 ± 0.1 |
| NDSC + glutaraldehyde | 71.6 |
| HAc-NHS blocked – HBDSC | 45.1 ± 0.2 |
| HBDSC + EDC/NHS | 60.4 ± 0.9 |
| HBDSC + JEFFAMINE D230 | 82.4 ± 0.5 |
| HBDSC + JEFFAMINE ED2001 | 74.9 ± 0.8 |

All materials were completely degraded within 72 hours, (NDSC and HBDSC even within 1 hour), except for the collagen disc crosslinked with JEFFAMINE D230 spacer. After 9 days, 29% of the initial weight was left. The stability of the JEFFAMINE D230-crosslinked collagen is significant when compared to the other crosslinked collagens, including the glutaraldehyde.

Water absorption experiments. The results displayed in Table 4, below, show that the employed crosslinking techniques generally tend to increase the wettability of the collagenous materials. This may be in contrast to what one would expect, since crosslinking typically would tighten the collagenous network so that entrance of water would be hampered.

TABLE 4

Results of water absorption experiment

| material type | time to complete wetting (seconds) | ratio wet weight/dry weight |
| --- | --- | --- |
| non-crosslinked – NDSC | 52–68 | 5.5 |
| NDSC + glutaraldehyde | 8–13 | 5.0 |
| HAc-NHS blocked – HBDSC | 38–46 | 5.9 |
| HBDSC + EDC/NHS | 5–7 | 6.5 |
| HBDSC + JEFFAMINE D230 | 5–7 | 6.2 |
| HBDSC + JEFFAMINE ED2001 | 3–4 | 5.1 |

Crosslinking involving the JEFFAMINE spacers shows the fastest rehydration, whereas glutaraldehyde crosslinking tends to be a bit slower. It is suggested that the highly hydrophilic crosslinked collagen-derived materials promote infiltration and diffusion of tissue fluid through the material matrix, providing supply of oxygen, nutritive substances, electrolytes and drainage of metabolites. Also, ing-rowth of capillary blood vessels and cells will be promoted, and consequently the healing response will be improved. In addition, hydrophilicity improves the blood compatibility of the material.

Evaluation of in vitro cytotoxicity. It has repeatedly been shown that glutaraldehyde crosslinked collagenous materials have cytotoxic characteristics through release of toxic glutaraldehyde-derived compounds. This was confirmed by Speer D. P., et al., J. Biomed. Mater. Res., 14, 753–764 (1980), who found that glutaraldehyde concentrations as low as 3 ppm inhibited fibroblast cell growth as measured by $H^3$-thymidine uptake. In vivo release of glutaraldehyde-derived substances is manifested by a persisting inflammatory reaction.

Cytotoxicity of collagenous samples was measured in a very sensitive in vitro test (Van Luyn M. J. A., Thesis, Rijksuniversiteit Groningen, Groningen, The Netherlands, 1992). In this test, glutaraldehyde-crosslinked collagen samples showed a cell growth inhibition of up to 80%, including presence of many cells with a deviant morphology; a severely cytotoxic material. Collagen samples crosslinked according to the method of the present invention using the JEFFAMINE D230 spacer showed a cell growth inhibition of 25%, while cells with a deviant morphology were not observed. According to the standards of this cytotoxicity test, this number correlates with a nontoxic to slightly cytotoxic material, which would be considered to have passed traditional cytotoxicity testing.

Subcutaneous rat implant study. Another characterization model is the acute implantation of crosslinked collagenous materials in rats. These first implant studies were primarily aimed at a first screening of in vivo behavior. Collagen crosslinked according to the method of the present invention using the JEFFAMINE D230 spacer was compared with glutaraldehyde crosslinked collagen.

Inflammatory response. The JEFFAMINE D230 collagen showed a very quiescent tissue response, with a thin, normal looking fibrous encapsulation of the entire disc. At day 1, the disc was completely infiltrated with granulocytes and macrophages; from day 5 on, formation of foreign body giant cells was observed; fibroblast in-growth was prominent and almost complete at day 10. The collagen matrix appeared very stable with hardly any signs of degradation; fibroblast activity resulted in neo-collagen formation, although it was not prominent.

The glutaraldehyde collagen showed a thicker and more active fibrous capsule. Increased cell infiltration and cell death of both neutrophils and macrophages was observed within the collagen disc. Cellular in-growth of all cell types including fibroblasts was less; in between collagen fibrils and infiltrated cells unoccupied spaces were observed and cell pseudopodia did not completely adhere to and surround bundles of collagen fibrils. Neo-collagen formation was not or hardly observed.

These results indicate that the material crosslinked by the present invention did not elicit an adverse inflammatory reaction, and was found to be biocompatible; thus confirming the earlier in vitro findings. The results demonstrate an improved biocompatibility compared to the glutaraldehyde collagen.

Calcification. The JEFFAMINE D230 collagen did not show any signs of calcification in the 6 weeks implant duration, both by von Kossa staining and TEM analysis.

On the contrary, glutaraldehyde crosslinked collagen did show calcification from day 10 on; at 3 weeks calcification had proceeded further showing large calcific deposits, and after 6 weeks completely calcified collagen structures were observed.

These results indicate that the disclosed crosslinking technology prevented the calcification of the implanted collagen material, which is a significant improvement over the glutaraldehyde collagen.

Crosslinking of Porcine Aortic Valves. The results of this experiment illustrate the significant difference between the minimal calcification of the leaflet-tissues fixed using the process of the present invention, and the high degree of calcification observed in the leaflets fixed using either the glutaraldehyde method or the EDC/NHS control. Calcium levels (in mg calcium per g dry tissue) in the porcine aortic valve leaflets by crosslinking method were: (1) 194.23; (2) 171.20; (3) 5.85; (4) 1.34; (5) 1.65; and (6) 2.22.

Significantly, a decrease in calcification levels in the aortic wall was also observed. The aortic wall seems to be far more prone to calcification than the leaflets, and in that respect the obtained results confirm that the process of the present invention is an improvement over the glutaraldehyde fixation method. Calcium levels (in mg calcium per g dry tissue) in the porcine aortic wall by crosslinking method were: (1) 112.60; (2) 96.40; (3) 63.23; (4) 49.17; (5) 92.50; and (6) 48.70.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed:

1. A method for making a bioprosthetic device made of collagen-based material having collagen amine groups and collagen carboxyl groups, the method comprising:
    blocking at least a portion of the collagen amine groups with a blocking agent;
    activating at least a portion of the collagen carboxyl groups after blocking at least a portion of the collagen amine groups to form activated carboxyl groups; and
    contacting the activated collagen carboxyl groups with a polyfunctional spacer to crosslink the collagen-based material.

2. The method of claim 1, wherein the blocking agent is selected from the group consisting of an acylating agent, an aminating agent, and a biologically active derivative thereof.

3. The method of claim 2 wherein the step of blocking comprises contacting the collagen amine groups with an acylating agent.

4. The method of claim 3, wherein the acylating agent is selected from the group consisting of an N-hydroxy succinimide ester, a p-nitrophenyl ester, 1-acetylimidazole, and citraconic anhydride.

5. The method of claim 4, wherein the acylating agent is selected from the group consisting of acetic acid N-hydroxysuccinimide ester, sulfo-NHS-acetate, propionic acid N-hydroxysuccinimide ester, p-nitrophenyl formate, p-nitrophenyl acetate, p-nitrophenyl butyrate, 1-acetylimidazole, and citraconic anhydride.

6. The method of claim 2 wherein the step of blocking comprises contacting the collagen amine groups with an aminating agent.

7. The method of claim 6 wherein the aminating agent is an aldehyde or a ketone.

8. The method of claim 7 wherein the aminating agent is a monofunctional aldehyde.

9. The method of claim 8, wherein the monofunctional aldehyde is selected from the group consisting of propanal, butanal, and hexanal.

10. The method of claim 6 wherein the step of blocking comprises contacting the collagen amine groups with an aminating agent in the presence of a reducing agent.

11. The method of claim 10 wherein the reducing agent is selected from the group of sodium cyanoborohydride, sodium borohydride, dimethylamine borane, trimethylamine borane, and morpholine borane.

12. The method of claim 1 wherein the collagen-based material comprises whole tissue.

13. The method of claim 1, wherein the bioprosthetic device is a heart valve.

14. The method of claim 1 wherein each step is carried out in an aqueous solution.

15. The method of claim 1 wherein the step of blocking comprises blocking at least about 75% of the collagen amine groups.

16. The method of claim 15 wherein the step of blocking comprises blocking at least about 80% of the collagen amine groups.

17. The method of claim 16 wherein the step of blocking comprises blocking at least about 90% of the collagen amine groups.

18. The method of claim 1, wherein the step of activating comprises contacting the collagen carboxyl groups with an activating agent selected from the group consisting of a carbodiimide, an azide, 1,1'-carbonyldiimidazole, N,N'-disuccinimidyl carbonate, 2-ethoxy-1-ethoxycarbonyl-1,2-dihydroquinoline, 1,2-benzisoxazol-3-yl-diphenyl phosphate, and N-ethyl-5-phenylisoxazolium-s'-sulfonate, and mixtures thereof.

19. The method of claim 18 wherein the activating agent is a carbodiimide.

20. The method of claim 19, wherein the carbodiimide is water soluble.

21. The method of claim 20 wherein the carbodiimide is 1-ethyl-3-(3-dimethylaminopropyl)carbodiimide.HCl.

22. The method of claim 19, wherein the carbodiimide is selected from the group consisting of 1-ethyl-3-(3-dimethylaminopropyl)carbodiimide.HCl, cyanamide, N,N'-dicyclohexylcarbodiimide, N,N'-diisopropylcarbodiimide, 1-cyclohexyl-3-(2-morpholinoethyl)carbodiimide metho-p-toluenesulfonate, and mixtures thereof.

23. The method of claim 1 wherein the step of activating comprises contacting the collagen carboxyl groups with an activating agent in the presence of a stabilizing agent.

24. The method of claim 23, wherein the stabilizing agent is selected from the group consisting of N-hydroxysuccinimide, N-hydroxybenzotriazole, N-hydroxy-5-norbornene-endo-2,3-dicarboximide, 4-dimethylaminopyridine, the sulfo-derivative of N-hydroxysuccinimide, and mixtures thereof.

25. The method of claim 23 wherein the step of activating comprises contacting the collagen carboxyl groups with a carbodiimide and N-hydroxysuccinimide.

26. The method of claim 1, wherein the step of reacting the activated collagen carboxyl groups with a polyfunctional spacer comprises reacting the activated collagen carboxyl groups with a polyfunctional spacer and a diamine spacer.

27. The method of claim 26 wherein the diamine spacer is hydrophilic.

28. The method of claim 27, wherein the diamine spacer is selected from the group consisting of polyethyleneglycol spacers, polypropyleneglycol spacers, polyethylene-propyleneglycol spacers, and mixtures thereof.

29. The method of claim 28 wherein the hydrophilic diamine spacer is represented by the following general formula:

wherein: x+z=0–70 and y=0–90.

30. The method of claim 29 wherein x+z=0–35 and y=0–45.

31. A method for crosslinking collagen-based material having collagen amine groups and collagen carboxyl groups, the method comprising:

blocking at least a portion of the collagen amine groups with a blocking agent to form blocked amine groups;

contacting the collagen-based material having the blocked amine groups with a polyfunctional spacer for a time sufficient for the spacer to penetrate the collagen-based material; and activating at least a portion of the collagen carboxyl groups of the collagen-based material toward the polyfunctional spacer to crosslink the collagen-based material.

32. The method of claim 31 wherein the step of blocking comprises contacting the collagen amine groups with an acylating agent.

33. The method of claim 32, wherein the acylating agent is selected from the group consisting of acetic acid N-hydroxysuccinimide ester, sulfo-NHS-acetate, propionic acid N-hydroxysuccinimide ester, p-nitrophenyl formate, p-nitrophenyl acetate, p-nitrophenyl butyrate, 1-acetylimidazole, and citraconic anhydride.

34. The method of claim 31 wherein the step of blocking comprises contacting the collagen amine groups with an aminating agent.

35. The method of claim 34 wherein the aminating agent is an aldehyde or a ketone.

36. The method of claim 31 wherein the step of blocking comprises blocking at least about 75% of the collagen amine groups.

37. The method of claim 31, wherein the step of activating comprises contacting the collagen carboxyl groups with an activating agent selected from the group consisting of a carbodiimide, an azide, 1,1'-carbonyldiimidazole, N,N'-disuccinimidyl carbonate, 2-ethoxy-1-ethoxycarbonyl-1,2-dihydroquinoline, 1,2-benzisoxazol-3-yl-diphenyl phosphate, and N-ethyl-5-phenylisoxazolium-s'-sulfonate, and mixtures thereof.

38. The method of claim 37 wherein the activating agent is a carbodiimide.

39. The method of claim 38 wherein the step of activating comprises contacting the collagen carboxyl groups with a carbodiimide and N-hydroxysuccinimide.

40. The method of claim 31 wherein the polyfunctional spacer is a hydrophilic bifunctional spacer.

41. The method of claim 31 wherein the hydrophilic spacer is represented by the following general formula:

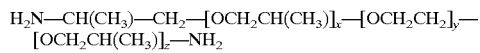

wherein: x+z=0–70 and y=0–90.

42. A method for crosslinking collagen-based material having collagen amine groups and collagen carboxyl groups, the method comprising:

blocking at least a portion of the collagen amine groups with a blocking agent to form blocked amine groups;

contacting the collagen-based material having the blocked amine groups with a hydrophilic bifunctional spacer represented by the following general formula:

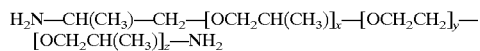

wherein: x+z=0–70 and y=0–90; and activating at least a portion of the collagen carboxyl groups of the collagen-based material toward the bifunctional spacer with a carbodiimide to crosslink the collagen-based material.

* * * * *